United States Patent [19]

Dzula et al.

[11] 4,018,089
[45] Apr. 19, 1977

[54] FLUID SAMPLING APPARATUS

[75] Inventors: Gregory Dzula, N. Caldwell, N.J.;
Melvin Levine, New York, N.Y.;
Elmer Ambrose Sperry, III,
Pompton Plains, N.J.

[73] Assignee: Beckman Instruments, Inc.,
Fullerton, Calif.

[22] Filed: May 5, 1976

[21] Appl. No.: 683,569

[52] U.S. Cl. .................................... 73/422 R
[51] Int. Cl.² .................................. G01N 1/14
[58] Field of Search ............ 73/422 R, 202, 212,
73/349, 61 R, 61.1

[56] References Cited

UNITED STATES PATENTS

| | | | |
|---|---|---|---|
| 2,481,882 | 9/1949 | Sebald | 116/117 R |
| 3,177,706 | 4/1965 | Shuman et al. | 116/117 R |
| 3,538,748 | 11/1970 | Linsell | 73/422 |
| 3,590,473 | 7/1971 | Carlson | 73/212 |
| 3,625,065 | 12/1971 | Thompson | 73/422 |

*Primary Examiner*—S. Clement Swisher
*Attorney, Agent, or Firm*—R. J. Steinmeyer; P. R. Harder; D. A. Streck

[57] ABSTRACT

Improved apparatus for bringing a fluid in a process stream in contact with a sensor is disclosed. The present invention uses the kinetic energy of the process fluid to convey some of the fluid to and from the sensor, as opposed to the prior art practice of inserting the sensor itself into the process fluid stream. A nozzle is placed into the process fluid stream facing into the direction of flow. A small portion of the flowing process fluid is trapped by the nozzle and some of its kinetic energy is converted to pressure. This pressure causes a flow from the nozzle into a conduit through an open valve to the sensor. The fluid continues past the sensor and returns to the process fluid stream through the same valve. In one embodiment, the path for incoming fluid and exiting fluid are separate paths. In a second embodiment, the incoming fluid and exiting fluid exist coaxially.

10 Claims, 6 Drawing Figures

FLUID SAMPLING APPARATUS

BACKGROUND OF THE INVENTION

The present invention relates to fluid sampling apparatus and more specifically to holding devices for sensors which are connected to a process fluid stream.

A typical prior art insertion type sensor is shown in FIG. 1. A sensor such as, for example, conductivity cell 10 is located at the end of a hollow shaft 12, as shown, so that conductivity cell 10 can be placed in the moving process fluid stream 14. In this position, a portion of the process fluid stream 14 passes across the conductivity cell 10 through openings 16 in hollow shaft 12. Wiring for the conductivity cell 10 passes through hollow shaft 12 to proper instrumentation. To prevent process fluid stream 14 from escaping from main process conduit 18 wherein it is located, hollow shaft 12 containing conductivity cell 10 is disposed within an outer conduit 20 having a packing gland 22 to prevent leakage and locking device 23 to hold hollow shaft 12 in place, located at the outer end thereof as shown. To allow removal of conductivity cell 10 for replacement or servicing, the common practice is to include a gate valve 24 in outer conduit 20. To remove the conductivity cell 10 from prior art apparatus as represented by FIG. 1, locking device 23 is loosened and hollow shaft 12 withdrawn to the point where the conductivity cell 10 is clear of gate 26 of gate valve 24 and still within packing gland 22. Gate valve 24 is then closed allowing hollow shaft 12 to be removed the rest of the way without the escape of process fluid stream 14. The re-installation of hollow shaft 12 is the reverse of the above described process. Obviously, this apparatus has certain limitations in addition to its two stage removal and insertion process. Not only is the length of the insertion rod (hollow shaft 12) a physical limitation in itself, but in addition, since it must be straight, this technique cannot be used to insert a sensor around a corner.

Another possible prior art technique is disclosed in FIG. 2. In this instance, a bypass path is created to divert a portion of a process fluid stream from the main process conduit 18 through bypass conduit 28 containing the sensor 11. To allow removal and re-insertion of the sensor 11 in such an arrangement, two valves 30 must be supplied to bracket the sensor 11 as shown.

DESCRIPTION OF THE PREFERRED EMBODIMENTS OF THE PRESENT INVENTION

Figure 1:
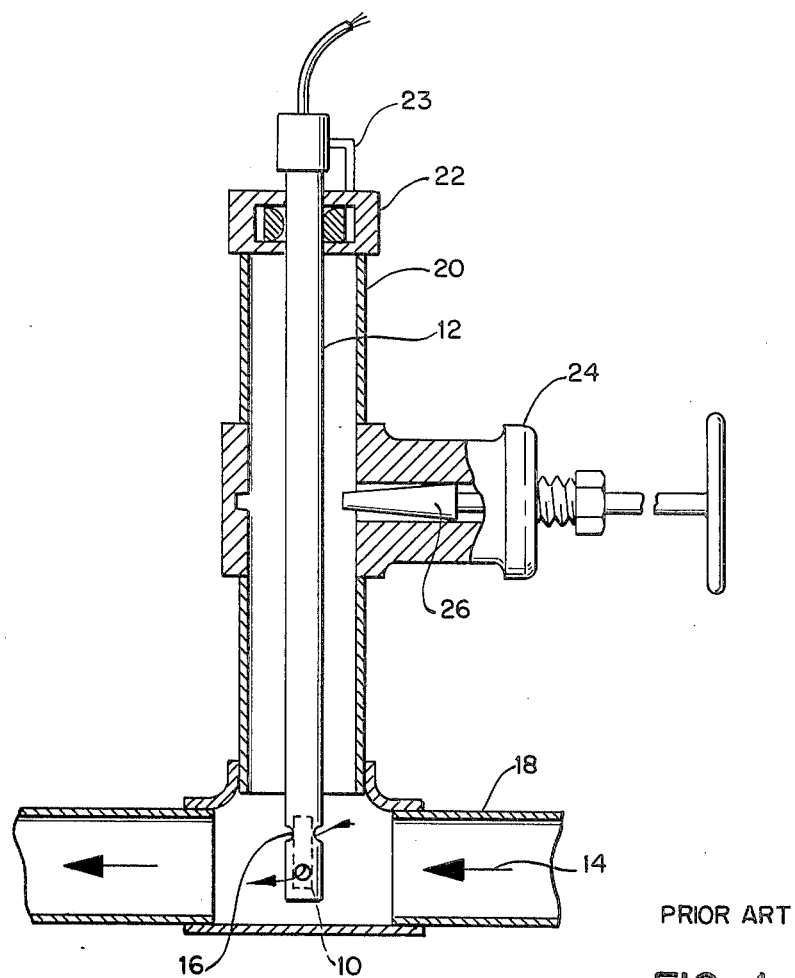
FIG. 1 is a cut-away elevation of an insertion type conductivity cell according to prior art techniques.
Figure 2:
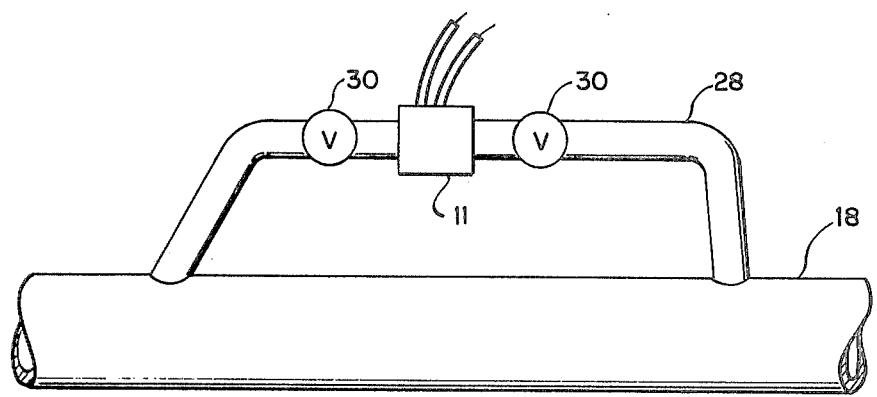
FIG. 2 is a representation of another prior art technique.
Figure 4:
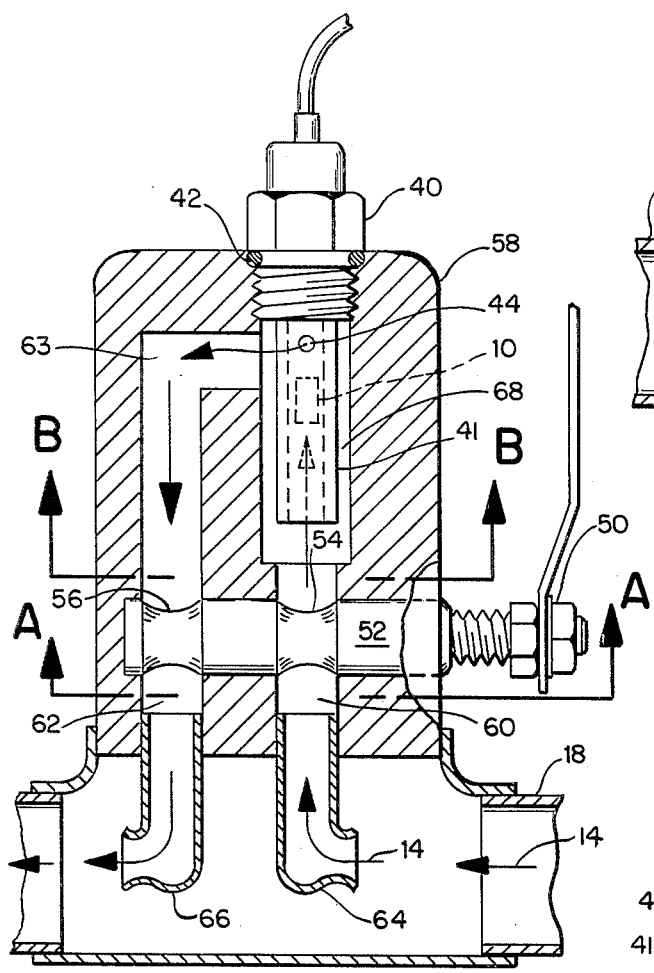
FIG. 4 is a cut-away elevation of an insertion type sampling and sensor holding device with a shut-off valve employing another embodiment of the present invention.
Figure 3:
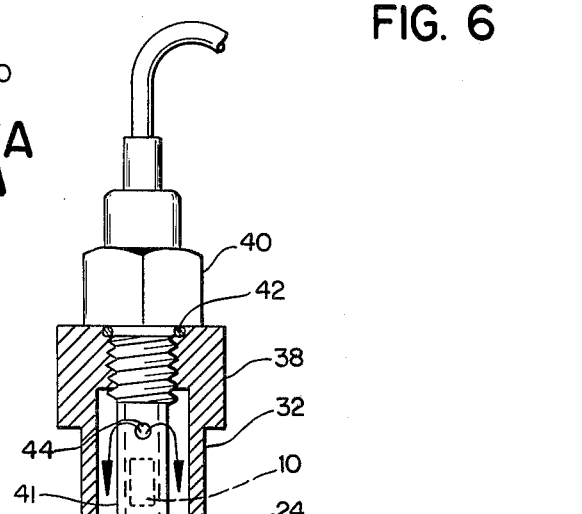
FIG. 3 is a cut-away elevation of an insertion type sampling and sensor holding device with a shut-off valve employing one embodiment of the present invention.

One embodiment of the present invention is illustrated in FIG. 3. A body, being an outer conduit 32, having a valve, such as gate valve 24, inserted therein is connected into a main process conduit 18 as shown. In the portion of outer conduit 32 between gate valve 24 and main process conduit 18, an inner conduit 34 is disposed terminating in a nozzle portion 36 facing into process fluid stream 14. Inner conduit 34 can be held in place in any convenient manner such as with pins or axial vanes (not shown). The cross-sectional area of the inner conduit 34 should be approximately equal to one-half the cross-sectional area of the outer conduit 32. By thus having flow paths of substantially equal area, equal quantities of fluid can move in one direction through inner conduit 34 and in the opposite direction through outer conduit 32 at the same time. The portion of outer conduit 32 from gate valve 24 away from main process conduit 18 terminates in holding means 38 removably holding sensor holder 40. While various methods of holding sensor holder 40 are possible, the easiest method is to thread sensor holder 40 and holding means 38 and provide an O-ring seal 42 as shown in FIG. 4. The portion of sensor holder 40 between holding means 38 on its inner side and gate valve 24 is a holder conduit 41 disposed to be on the opposite side of gate valve 24 from inner conduit 34, forming a continuation thereof, substantially in coaxial alignment therewith and having substantially the same cross-sectional area. The holder conduit 41 of sensor holder 40 has the sensor 10 disposed therein and exit holes 44 in the walls thereof. Both the exit holes 44 and the sensor 10 are sized and positioned such that fluid entering holder conduit 41 adjacent gate valve 24 will flow across sensor 10 and out exit holes 44 without substantially impeding the flow of the fluid. Thus, a passageway is formed between the openings of inner conduit 34 and outer conduit 32 where fluid can enter from the process fluid stream 14 through nozzle 36, pass through the passageway and exit to the process fluid stream 14 through the opening of outer conduit 32. As can be seen, this passageway is closable in two locations by the gate actuator 45 of gate valve 24.

In operation, with gate valve 24 in its open position as shown in FIG. 3, process fluid stream 14 moves along main process conduit 18. A portion of process fluid stream 14, as indicated by incoming arrows 46, is forced up inner conduit 34 by the kinetic energy of process fluid stream 14 at the nozzle portion 36. The kinetic energy forces the fluid in the direction of incoming arrows 46 across open gate valve 24 and into the coaxially aligned opening of holder conduit 41. The fluid flows across sensor 10 and out exit holes 44 into outer conduit 32 where it flows between the outside of inner conduit 34 and the inner wall of outer conduit 32 in the direction of outgoing arrows 48. It then bridges the gap created by open gate valve 24 and continues in the direction of outgoing arrows 48 until it rejoins the moving process fluid stream 14 in main process conduit 18 adjacent nozzle portion 36. To service the sensor 10, gate valve 24 need only be closed and sensor holder 40 can be immediately removed in a one-step operation. Since the sensor holder 40 does not pass through the gate valve 24 as in the prior art devices, the portion of inner conduit 34 and outer conduit 32 between gate valve 24 and main process conduit 18 need not be straight and can be of substantially any length. To minimize turbulence in the area of gate valve 24, the gap between inner conduit 34 and the holder conduit 41 of conductivity cell holder 40 should be minimized. One technique to accomplish this will be described later in connection with FIG. 5.

An alternate embodiment of noncoaxial construction is shown in FIG. 4. In this embodiment, the gate valve 24 is replaced with a rotary plug valve 50 of the type which completely blocks a passage in one position and provides an unhindered path when the plug actuator 52 is rotated 90°. The plug actuator 52 of the embodiment of FIG. 4 contains a first valve opening 54 and a second valve opening 56. While the description of the embodiment of FIG. 4 that follows is directed to a unitary construction as shown in FIG. 4, it is to be understood that the apparatus could be separated at either line A—A or B—B and the separated portion removed at any distance to be interconnected to the portion remaining at the main process conduit 18 by two conduits.

Body 58 is mounted on main process conduit 18. Body 58 has a first conduit opening 60 and a second conduit opening 62 to the interior of main process conduit 18. First conduit opening 60 has a first nozzle 64 affixed thereto facing into process fluid stream 14. Second conduit opening 62 has a second nozzle 66 affixed thereto facing opposite the process fluid stream as shown in FIG. 4. The plug actuator 52 of rotary plug valve 50 is positioned within body 58 such that first valve opening 54 is transverse of conduit 63 in a first location and second valve opening 56 is transverse of conduit 63 in a second location as shown. Thus, a passageway between the two oenings 60, 62 into the main process conduit 18, being closable in two locations by valve 50, is again formed as in the case of the embodiment of FIG. 3. When rotary plug valve 50 is in the open position, the conduit 63 is free to have fluid pass therethrough. When rotary plug valve 50 is in the closed position, conduit 63 is blocked by plug actuator 52 in both locations such that fluid is unable to pass therethrough. The portion of conduit 63 between first valve opening 54 and second valve opening 56 contains a chamber 68. A sensor holder 40 such as that used in the embodiment of FIG. 3 is removably mounted into chamber 68 such that fluid entering chamber 68 through conduit 63 from first valve opening 54 will be directed into the holder conduit 41 of sensor holder 40, pass over sensor 10 and leave through exit holes 44. The fluid then continues through conduit 63 and out second nozzle 66 to return to the process fluid stream 14. As with the embodiment of FIG. 3, to remove the sensor holder 40, the valve 50 need only be moved from the open to closed position and sensor holder 40 can be removed directly.

Figure 5:
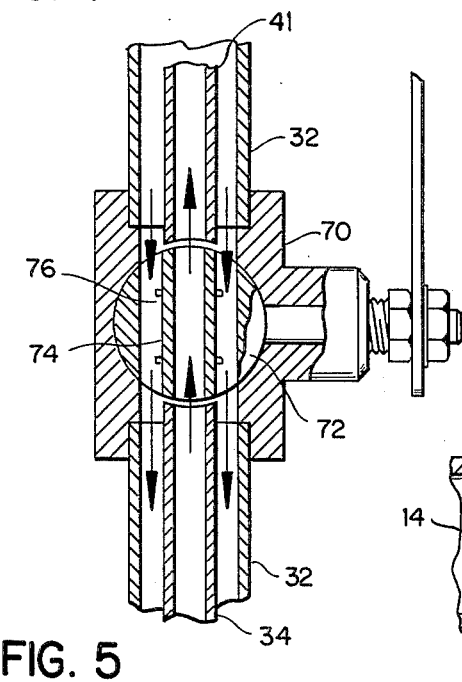
FIG. 5 is a cut-away elevation through an alternate valve arrangement in the apparatus of FIG. 3.

Referring to FIG. 5, an alternate valving arrangement is shown which minimizes the turbulence in the valve area in an embodiment such as that shown in FIG. 3. A ball or plug valve 70 can be used in place of the gate valve of FIG. 3. The ball actuator 72 of valve 70 is constructed with a bridging conduit 74 fastened inside the cylindrical passage 76 of ball actuator 72. Cylindrical passage 76 should be the same cross-sectional area as outer conduit 32. Bridging conduit 74 should be the same cross-sectional area as inner conduit 34 and can be fastened inside cylindrical passage 76 in the same manner as inner conduit 34 is fastened within outer conduit 32. In the closed position, ball actuator 72 blocks fluid flow to and from sensor holder 40 in the conventional manner of a ball or plug valve, thus again closing the formed passageway in two locations. When rotated 90° to the open position, bridging conduit 74 aligns axially with holder conduit 41 and inner conduit 34 and bridges substantially the entire distance between the two, forming a virtually uninterrupted passageway.

Figure 6:
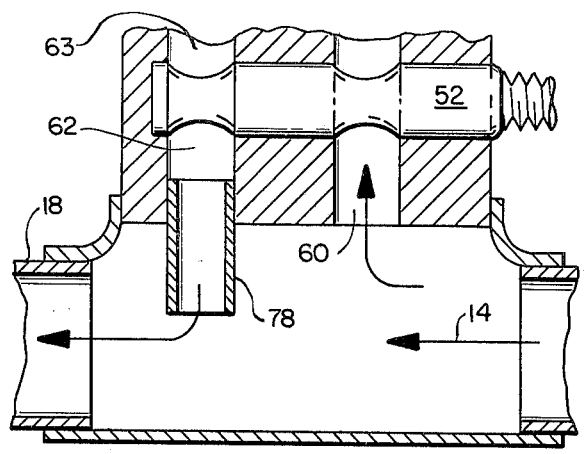
FIG. 6 is a cut-away elevation through a portion of an embodiment such as that of FIG. 4 employing an alternate nozzle arrangement.

In the preferred embodiment, the fluid from the process stream 14 enters through a nozzle facing into the moving stream as with nozzle 36 of FIG. 3 or first nozzle 64 of FIG. 4. In an alternate technique, applicable to both the embodiment of FIG. 3 and the embodiment of FIG. 4, a single nozzle is placed with an opening crosswise to the flow of moving process stream 14 near the center of main process conduit 18. Referring first to FIG. 6, the embodiment of FIG. 4 is shown adapted to this approach. A nozzle conduit 78 is placed in the most downstream opening of conduit 63, second conduit opening 62. Nozzle conduit 78 extends from second conduit opening 62 to a point approximately in the center of main process conduit 18 and has an opening at that point crosswise to the flow of process stream 14. The fluid of process stream 14 flows slightly faster in the center of main process conduit 18 than adjacent the walls thereof due to the boundary layer effects at the walls. Thus, as the process fluid stream 14 flows across first opening 60 and nozzle conduit 78, a lower pressure will exist at the opening to nozzle conduit 78 than at first opening 60. These unequal pressures at the two ends of conduit 63 will cause a portion of process fluid stream 14 to enter first opening 60, pass through conduit 63, and exit back into the balance of process fluid stream 14 through nozzle conduit 78.

Referring now to FIG. 3, if the nozzle portion 36 of inner conduit 34 were severed and removed at the line marked C—C, the apparatus would be adapted to operate in the same manner as just described in relation to the embodiment of FIG. 4. Note, however, that if reconfigured in this manner, the flow through the passageway between the openings of inner conduit 34 and outer conduit 32 will be the reverse of that previously described in relation to the operation of the apparatus of the embodiment of FIG. 3. Because of the faster fluid flow across the opening of inner conduit 34, when severed at line C—C, the lower pressure point will exist at the opening to inner conduit 34. Consequently, a portion of process fluid stream 14 will be drawn into outer conduit 32 (opposite the direction of arrows 48), pass through the passageway, and exit through inner conduit 34. If this embodiment were constructed, the valve arrangement of FIG. 5 would be preferred as there would be a tendency for the fluid to pass from outer conduit 32 into inner conduit 34 in the space of valve 24, thus bypassing the sensor 10, if the gate valve 24 of FIG. 3 were employed. The ball valve 70 of FIG. 5 presents a substantially continuous passageway that would eliminate this problem.

SUMMARY OF THE INVENTION

While the present invention has been described with reference to a conductivity cell and employing specific valving configurations, it is to be understood that the invention is an insertion type sampling device combined with a sensor holder and a single valve. It provides a novel apparatus that can be inserted into a process stream at a single point such as with a pipe "tee" for removing a sample from and returning the sample to the process stream. It provides means for holding a sensor and exposing it to the sample as well as means for isolating the sensor for removal. This is accomplished by apparatus having a nozzle placed into the process fluid stream to trap a portion of the moving fluid. The kinetic energy of the moving stream is used to force the sample into a passageway, through an open valve to the sensor, past the sensor and back to the process fluid stream through the same valve. The paths of the sample through the passageway to and from the sensor and through the valve can exist coaxially or separately.

Having thus described our invention, we claim:

1. Improved insertion type sampling apparatus for sampling a moving fluid in a main conduit comprising:
   a. a body adapted to be mounted on the main conduit and having a first opening and a second opening into the interior of the main conduit, said body further having a passageway therein communicating on one end with said first opening and communicating on the other end with said second opening whereby fluid can enter said passageway from said main conduit through one of said openings, flow through said passageway and re-enter the fluid in the main conduit through the other of said openings, the portion of said passageway up to said means for holding a sensor and the portion of said passageway after said means for holding a sensor being a pair of conduits one within the other;
   b. first nozzle means connected to said first opening and being disposed with an opening in the moving fluid whereby the kinetic energy of the moving fluid will force a portion of the fluid through said passageway;
   c. valve means operably attached to said body and being adapted to open and close said passageway in two locations with one movable actuator; and,
   d. means for holding a sensor disposed between said two locations of valve opening and closing in said passageway and being so shaped and positioned that when said valve means is in the open position a portion of the fluid passing through said passageway will contact a sensor held by said holding means.

2. Improved insertion type sampling apparatus as claimed in claim 1 wherein:
   the inner conduit portion of said passageway contains a discontinuity to allow the actuator of said valve means to pass therethrough.

3. Improved insertion type sampling apparatus as claimed in claim 1 wherein:
   the cross-sectional area of the inner conduit of said passageway is substantially equal to one-half the cross-sectional area of the outer conduit of said passageway.

4. Improved insertion type sampling apparatus for sampling a moving fluid in a main conduit comprising:
   a. an outer conduit adapted on one end for mounting through the wall of the main conduit;
   b. means for holding a sensor disposed on the other end of said outer conduit, said sensor holding means being adapted to close said other end of said outer conduit and hold a sensor disposed inside said outer conduit;
   c. valve means operably connected in said outer conduit between said end mounted through the wall of the main conduit and said sensor holding means;
   d. a first inner conduit disposed within said outer conduit and extending from adjacent said valve means on one end to the main conduit on the other end, said inner conduit being positioned to direct fluid emerging from said end adjacent said valve means across a sensor being held by said sensor holding means; and,
   f. first nozzle means connected to said end of said first inner conduit adjacent the main conduit and being disposed with an opening facing into the moving fluid whereby the kinetic energy of the moving fluid will force a portion of the fluid into said first inner conduit.

5. Improved insertion type sampling apparatus as claimed in claim 4 wherein:
   said valve means is a gate valve, the gate actuator of said gate valve blocking both the path from said sensor holding means through said outer conduit and the path between said first inner conduit and a sensor being held in said holding means when said gate actuator is in the closed position.

6. Improved insertion type sampling apparatus as claimed in claim 4 and additionally comprising:
   a second inner conduit disposed within said outer conduit between said sensor holding means and said valve means and being positioned to receive fluid emerging from said first inner conduit and direct the fluid across a sensor being held by said sensor holding means.

7. Improved insertion type sampling apparatus as claimed in claim 6 wherein:
   said valve is a ball valve having a bridging conduit disposed within the cylindrical passage in the ball-actuator of said ball valve, said bridging conduit being positioned to direct fluid emerging from said first inner conduit through said valve and into said second inner conduit.

8. Improved insertion type sampling apparatus for sampling a moving fluid in a main conduit comprising:
   a. a body having a conduit therethrough, said conduit having an inlet and an outlet, said body being adapted to be mounted through the wall of a main conduit with said inlet and said outlet on the inside of the main conduit;
   b. valve means disposed within said body transverse said conduit in two places and adapted to be operated from outside said body, said valve means having an actuator blocking said conduit to the passage of fluid in two places when said valve means is in the closed position;
   c. means for holding a sensor disposed in said body and communicating with said conduit between said two points of valve blockage, said holding means being adapted to hold a sensor in said conduit whereby fluid flowing through said conduit will flow across the sensor; and,
   d. first nozzle means connected to said inlet and being disposed with an opening facing into the moving fluid whereby the kinetic energy of the moving fluid will force a portion of the fluid through said conduit.

9. Improved insertion type sampling apparatus as claimed in claim 8 and additionally comprising:
   second nozzle means connected to said outlet and being disposed with an opening facing opposite the direction of the moving fluid whereby fluid returning to the moving fluid in the main conduit can do so with minimum turbulence and interference with the fluid entering said first nozzle means.

10. Improved insertion type sampling apparatus as claimed in claim 8 wherein:

said sensor holding means has a holding conduit portion wherein a sensor is held, said holding conduit having an open end extending into said body conduit toward said inlet and exit holes disposed to cause fluid entering said holding conduit through said open end to pass over a sensor held therein and flow out said exit holes back into said body conduit.

* * * * *